(12) United States Patent
Andersen

(10) Patent No.: US 6,676,618 B2
(45) Date of Patent: Jan. 13, 2004

(54) ANKLE-FOOT ORTHOSIS AND A METHOD FOR MAKING THE SAME

(76) Inventor: Henrik Spang Andersen, Esrumvej 453, Graæsted, DK 3230 (DK)

( * ) Notice: Subject to any disclaimer, the term of this patent is extended or adjusted under 35 U.S.C. 154(b) by 97 days.

(21) Appl. No.: 09/804,449

(22) Filed: Mar. 12, 2001

(65) Prior Publication Data

US 2001/0031935 A1 Oct. 18, 2001

Related U.S. Application Data

(60) Provisional application No. 60/200,029, filed on Apr. 26, 2000.

(30) Foreign Application Priority Data

Mar. 14, 2000 (DK) .......................... 2000 00411

(51) Int. Cl.[7] ................ A61F 5/14; A61F 5/37
(52) U.S. Cl. ................ 602/7; 602/23; 602/27; 128/882
(58) Field of Search .............. 602/23, 27, 5–7; 128/882; 264/222–223, DIG. 30

(56) References Cited

U.S. PATENT DOCUMENTS

| | | | | |
|---|---|---|---|---|
| 2,558,986 A | * | 7/1951 | Seelert ................. 602/23 |
| 2,949,111 A | | 8/1960 | Ruotoistenmaki | |
| 3,680,549 A | | 8/1972 | Lehneis et al. | |
| 4,454,871 A | * | 6/1984 | Mann .................. 602/6 |
| 5,088,480 A | * | 2/1992 | Wang .................. 602/23 |
| 5,368,549 A | * | 11/1994 | McVicker ............. 602/6 |
| 5,624,386 A | * | 4/1997 | Tailor et al. ........... 602/16 |
| 5,897,515 A | | 4/1999 | Willner et al. | |
| 6,019,741 A | * | 2/2000 | Prieskorn ............. 602/5 |
| 6,146,344 A | * | 11/2000 | Bader ................. 602/6 |
| 6,146,349 A | * | 11/2000 | Rothschild et al. ...... 602/27 |
| 6,245,035 B1 | * | 6/2001 | Schrijver ............. 602/27 |
| D457,639 S | * | 5/2002 | McCoy ................ D24/192 |

FOREIGN PATENT DOCUMENTS

| | | |
|---|---|---|
| DE | 3804321 | 8/1989 |
| WO | WO9531950 | 11/1995 |

* cited by examiner

*Primary Examiner*—Danton D. DeMille
(74) *Attorney, Agent, or Firm*—Klein, O'Neill & Singh, LLP

(57) ABSTRACT

An ankle-foot orthosis is made integrally from a thin, shaped lightweight material. The orthosis comprises a flat foot-supporting member for extending beneath the sole of a foot of a user, a calf abutment member for abutting the calf of the user, a narrow connecting member extending from the foot-supporting member at a location on one side, preferably the outer side, of the ankle of the user to the calf abutment member so as to interconnect the foot-supporting member and the calf abutment member, and a releasable fastener for fastening the calf abutment member to a leg of the user. The orthosis may be made by a method, in which a thermoplastic material with reinforcing fibers is arranged between opposite plastic films or foils in a desired mutual arrangement. Thereafter, the space defined between the opposite films is sealed, and air or gas is then removed from the sealed space so as to compact the material arranged therein and so as to form a blank. The blank thus formed is thereafter heated to a plasticizing temperature and formed into the desired shape.

14 Claims, 4 Drawing Sheets

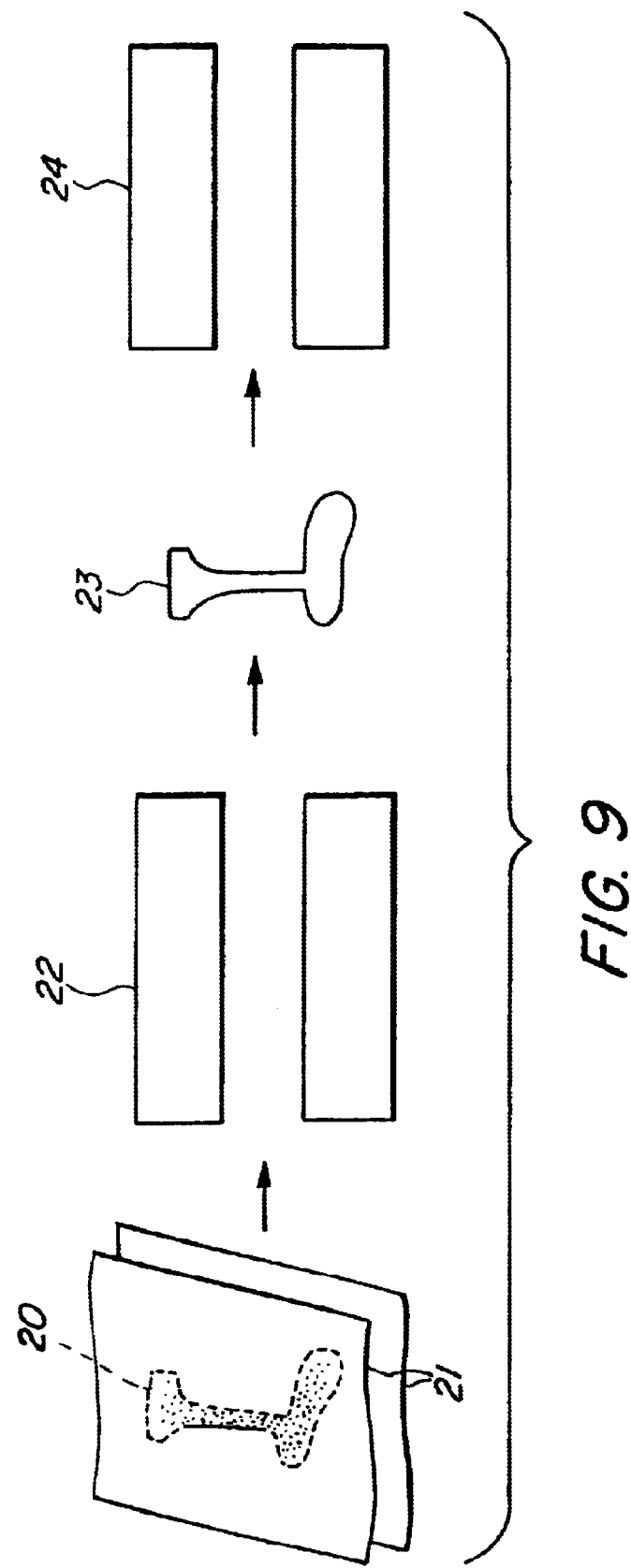

ANKLE-FOOT ORTHOSIS AND A METHOD FOR MAKING THE SAME

CROSS-REFERENCE TO RELATED APPLICATION

This application claims the benefit, under 35 U.S.C. Section 119(e), of provisional application No. 60/200,029; filed Apr. 26, 2000.

BACKGROUND OF THE INVENTION

1. Field of the Invention

The present invention relates to an ankle-foot orthosis made integrally from a thin, shaped lightweight material. Such orthosis is used for supporting the foot of a patient suffering from neurological disorders due to cerebral haemorrhage, tumours, radiation treatment or diseases, so that the patient may achieve an almost natural and dynamic gait.

2. Description of Prior Art

U.S. Pat. No. 5,897,515 discloses an orthosis of this kind made from carbon fibre reinforced plastic resin. The known orthosis comprises a foot plate for supporting the foot of the user and a frame part extending upwardly from the foot plate in front of and in contact with the tibia area of the leg of the user.

It is an object of the present invention to improve this known orthosis.

SUMMARY OF THE INVENTION

Thus, the present invention provides an ankle-foot orthosis made from a thin, shaped lightweight material and comprising a flat foot-supporting member for extending beneath the sole of a foot of a user, a calf abutment member for abutting the calf of the user, a narrow connecting member extending from the foot-supporting member at a location on one side—preferably the outer side—of the ankle of the user to the calf abutment member so as to interconnect the foot-supporting member and the calf abutment member without contacting the tibia area, and a releasable fastener for fastening the calf abutment member to a leg of the user.

Because the orthosis according to the invention does not comprise parts covering the front part or the tibia area of the leg of the user the orthosis according to the invention is less visible in use than the prior art devices. This feature is especially important when a female user wears a gown or skirt and uses the orthosis at the same time. Furthermore, the orthosis according to the invention is more comfortable in use than the orthosis disclosed in the above U.S. patent. The reason is that the known orthosis relies on contact with the tibia area, which is often tender or painful.

Preferably, the connecting member is connected to an arch part of the foot-supporting member at a location adjacent to the arch of the foot of the user and in front of the lateral malleole. From this position the narrow connecting member extend to the calf abutment member without passing the anterior or front side of the leg of the user. Thus, the connecting member preferably extends along a substantially helical path.

The connecting member is preferably relatively thin, narrow and stiff, while the calf abutment member is relatively broad and defines a relatively large abutment surface. Therefore, the narrow connecting member is preferably widening towards the calf abutment member, which is arched so as to define a calf abutment surface being substantially complementary to the shape of the calf of the user.

The releasable fastener used for fastening the orthosis to the leg of the user may be of any suitable kind and may, for example, comprise a skin adhesive, a clamp or the like. In the preferred embodiment the releasable fastener comprises a strap for interconnecting opposite ends of the calf abutment member. Thus, the calf abutment member and the strap may encircle the crus of the user, and tightening the strap may fasten the orthosis. The strap may be held in position for example by means of a Velcro fastener.

The orthosis according to the invention may be made from a thin material, such as sheet metal or plastic material. In the preferred embodiment, however, the orthosis is made from fibre-reinforced thermoplastic material. This allows for a lightweight and strong structure, and yet the form of the orthosis may to some extent be adapted to the individual user when the thermoplastic material is heated to a softening temperature. The reinforcing fibres may be of any type conventionally used in plastic materials. Preferably, carbon fibres, glass fibres or a combination of such fibres are used. The reinforcing fibres may form strands, layers or cloths. In these layers the fibres may extend in the same general direction, in two crossing directions or may be randomly distributed.

The arch part of the foot-supporting member may be located between a rear or a heel supporting part and a front or ball supporting part of the foot-supporting member, and the heel supporting part is then preferably more flexible than the ball supporting part. This may, for example, be obtained by including more layers of reinforcing fibres in the ball supporting part than in the heel supporting part. By varying the flexibility of the various parts of the foot-supporting member the user may obtain a more natural gait.

While it is important that the foot-supporting member is flexible the object of the connecting member is to maintain the foot-supporting member and the calf abutment member in a substantially fixed mutual position. Therefore, the connecting member is preferably substantially more stiff than the foot-supporting member. This may, for example be obtained by including more layers of reinforcing fibres in the connecting member than in the heel and ball supporting parts of the foot-supporting member.

At least some and preferably all of the layers of reinforcing fibres extending longitudinally within the connecting member may continue into the arch part of the foot-supporting member. This provides a good mutual connection between the connecting member and the foot-supporting member and also provides a desired reduced flexibility of the arch part.

The thermoplastic material forming the matrix material in which the reinforcing fibres are embedded is preferably one or more of the following materials: polyethylene, polypropylene, modified polyethylene terepthalate, polyamide, polyethylene terepthalate, polyether imide, polyether sulfone, and polyether ketone.

The orthosis according to the invention may be an undivided, unitary member. Alternatively, the orthosis may be made in two or more parts, which are subsequently interconnected permanently or releasably. As an example, the narrow connecting member may be divided into two parts, which are releasably interconnected, for example by means of a connecting member embracing adjacent ends of the said two parts of the narrow connecting member.

The connecting member may be adapted to allow the length of the narrow connecting member to be adjusted.

According to a further aspect the present invention provides a method of making an orthosis as described above, said method comprising positioning the thermoplastic material—preferably in the form of fibres, films, granules, or the like—and the reinforcing fibres between opposite plastic films or foils in a desired mutual arrangement, sealing the space defined between the opposite films, removing air or gas from said sealed space so as to compact the material arranged therein and form a blank. Subsequently, the blank thus formed may be formed into a desired shape, for example in a mould. This shape may be retained by heating the blank to a plasticizing temperature and subsequently cooling the shaped article thus formed. Preferably, such heating and cooling takes place while the shaped article is still within the mould. The said plasticizing temperature is preferably sufficiently high to allow the reinforcing fibres to become embedded in the plasticized thermoplastic material forming a matrix material.

The melting point of the films enclosing thermoplastic material and the reinforcing fibres may have a melting point being higher than the melting point of the thermoplastic material forming the matrix material. In that case the opposite films may form an outer skin layer of the finished orthosis. If, however, the melting point of the films is equal to or lower than that of the thermoplastic material positioned therebetween the material of the films may migrate into or become combined with the thermoplastic matrix material.

The air or gas may at least partly be removed from the sealed space between the opposite films, when positioned within the mould so as to remove residual air or gas or gas released during heating the thermoplastic material. Thus, the blank may be positioned in a mould cavity defined between a pair of first and second mould surfaces. The first mould surface defining the desired shape may be formed by a relatively stiff mould wall, while the second mould surface may be formed by a flexible wall and the mould cavity may then be connected to a vacuum source so as to form the blank into the desired shape.

Alternatively, a blank or pre-form formed by fibres and thermoplastic material may be arranged within a mould cavity defined between a pair of separable mould parts. When the pre-form or blank has been positioned in the mould cavity and heated to a plasticizing temperature the mould parts defining the desired shape of the final orthosis are pressed together so as to force the pre-form to adopt the shape defined by the mould cavity surfaces. At least one of the mould parts may be made from an elastic or resilient material, such as silicon rubber.

In any of the methods for making the orthosis, in which the blank or pre-form is heated, such heating may at least partly be obtained by placing electrical conducting material within the blank or pre-form and by sending electric current through the conducting material. Such conducting material may comprise reinforcing fibres, such as carbon fibres arranged within the blank or pre-form.

BRIEF DESCRIPTION OF THE DRAWINGS

The invention will now be further described with reference to the drawings, wherein:

FIG. 9 diagrammatically illustrates a method for producing the orthosis shown in FIGS. 1–4.

DETAILED DESCRIPTION OF THE PREFERRED EMBODIMENT

Figure 1:
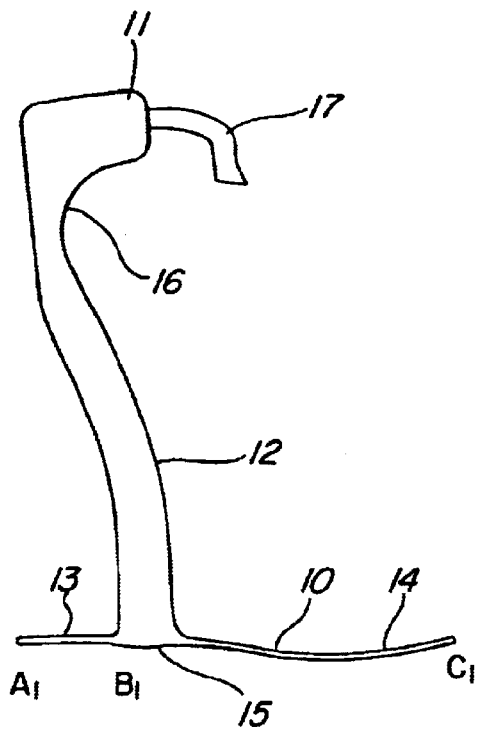
FIG. 1 is a side view of an embodiment of the orthosis according to the invention.
Figure 2:
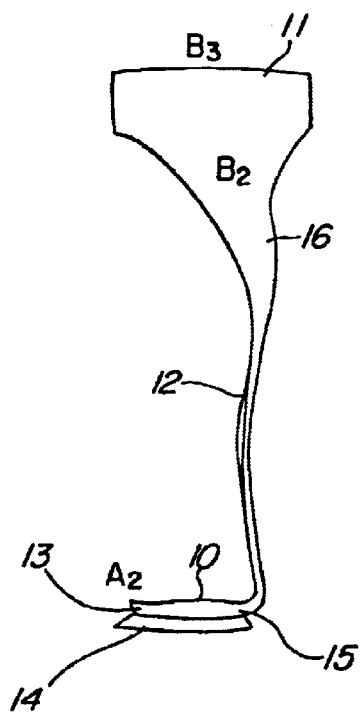
FIG. 2 is a rear view of the orthosis shown in FIG. 1.
Figure 3:
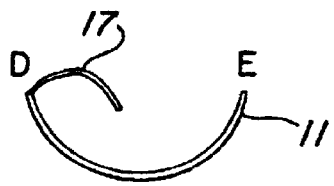
FIG. 3 is a top plan view showing the upper end of the orthosis.
Figure 4:
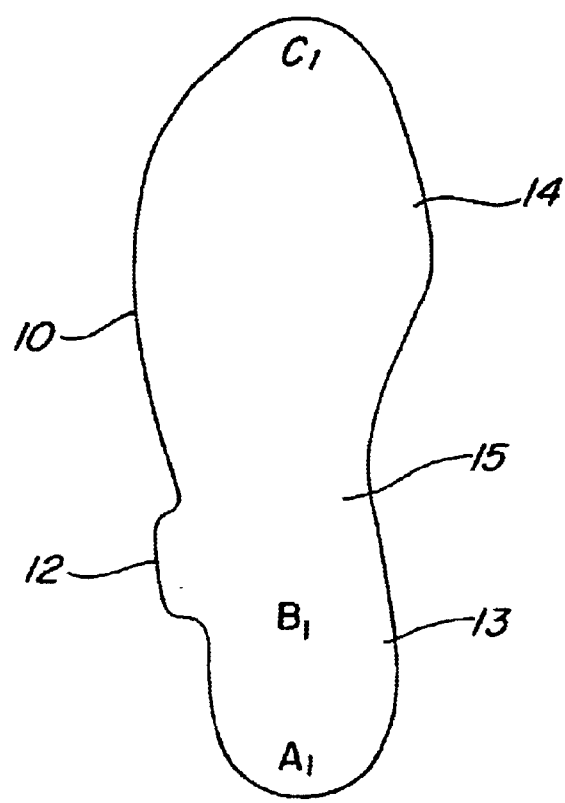
FIG. 4 is a bottom view of the orthosis.

FIGS. 1–4 illustrate an orthosis formed integrally from a fibre reinforced thermoplastic material. The orthosis comprises a substantially flat foot-supporting member or foot plate 10, a curved calf abutment member 11, and a narrow connecting member 12 interconnecting the foot-supporting member 10 and the calf abutment member 11. The foot-supporting member 10, which is adapted to be positioned under the sole of the foot of a user, has a rear heel supporting part 13, a front ball supporting part 14 and a connecting arch part 15 to be positioned below the arch of the foot of the user. The lower end of the narrow connecting member 12 is formed integrally with one side of the arch part 15 of the foot plate 10, and from this position the connecting member extends upwardly along the outer side and along the back side of the leg of the user along a substantially helical path. The upper end portion 16 of the connecting member 12 widens towards and is formed integrally with the calf abutment member 11.

One end of the calf abutment member 11 is provided with a fastening strap 17 and the free end of this strap may be fastened to the opposite end of the abutment member 11, for example by means of Velcro fasteners, not shown.

It should be understood that neither the connecting member 12 nor the calf abutment member 11 of the orthosis shown in the drawings and described above is in contact with the front part or the tibia of a leg of a user on which the orthosis has been mounted.

The various parts of the orthosis shown in the drawings and even the various parts of the foot plate 10 preferably have different flexibility in order to allow the user to walk more naturally. Such different flexibility may, for example, be obtained by using different numbers of layers and/or types of reinforcing fibres in the various parts of the orthosis.

Figure 5:
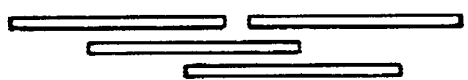
FIG. 5 illustrates diagrammatically and in an enlarged scale a sectional view of an arrangement of layers of reinforcing fibres extending from the location $A_1$ to the location $C_1$ in FIG. 4.
Figure 6:
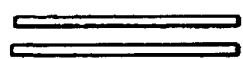
FIG. 6 illustrates diagrammatically and in an enlarged scale a sectional view of an additional arrangement of layers of reinforcing fibres extending from the location $B_1$ to the location $C_1$ in FIG. 4.

As an example, the foot plate 10 may contain four layers of reinforcing fibres extending from positions A1 to $C_1$ (indicated in FIGS. 1 and 4), while the part of the foot plate extending between positions $B_1$ and $C_1$ may contain two further layers. This means that the heel supporting part 13 will be more flexible than the other parts of the foot plate 10. FIG. 5 illustrates the mutual positions of the said four layers arranged in the foot plate 10. It should be noted that two upper layers are arranged in the same plane, but transversely separated. FIG. 6 illustrates the said two further layers, and it will be noted that these layers are positioned along the longitudinal axis of the foot plate 10.

Eight layers of reinforcing fibres may extend from position $A_2$ to position $B_3$ (FIG. 2), which means transversely to the foot plate 10 at the arch part 15 and along the connecting member 12 right to the upper rim of the abutment member 11. One additional layer, which is folded so as to form two additional layers having half width, may extend from the position $A_2$ to the position $B_2$ immediately below the calf abutment member 12. Finally, the calf abutment member 12 may contain two further layers of reinforcing fibres extending peripherally between the points D and E shown in FIG.

3. From the above it will become apparent that the arch part 15 of the foot-supporting element or foot plate 10 and the connecting part 12 are relatively stiff, while the calf abutment member 11 is rather flexible.

Figure 7:
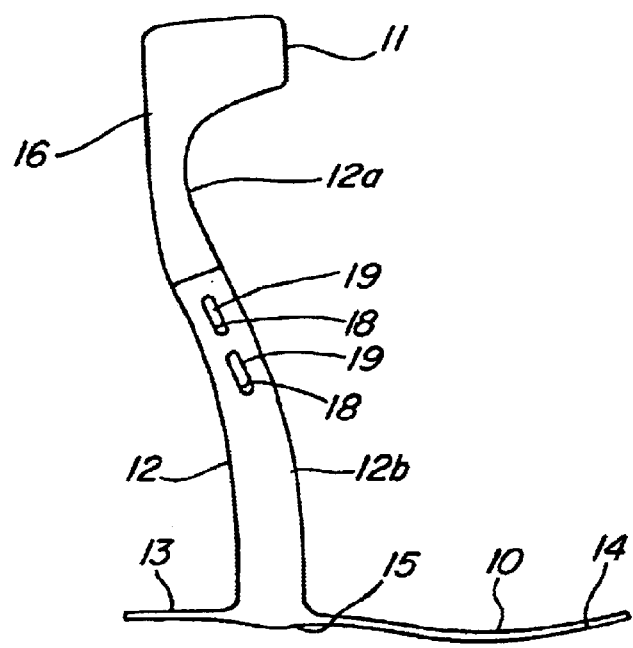
FIGS. 7 and 8 are side and rear views of a second embodiment of the orthosis according to the invention.
Figure 8:
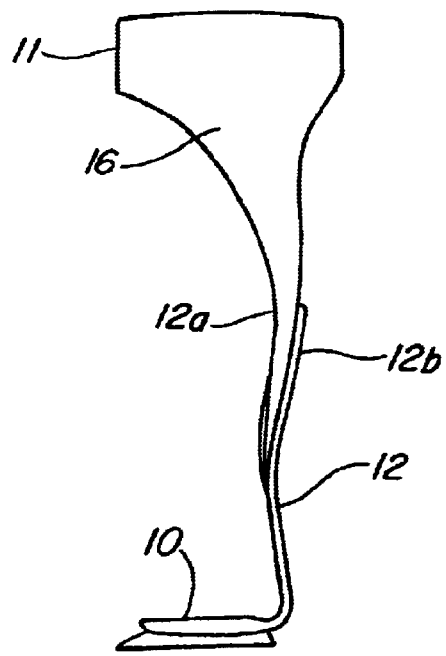

FIGS. 7 and 8 shows an embodiment of the orthosis having a narrow connecting member 12, which has been made in two parts 12a and 12b. The mutually overlapping end portions of these parts have subsequently been releasably interconnected by releasable connecting means, which may comprise studs 18 formed on the connecting member part 12a and engaging with slits or slots 19 formed in the connecting member part 12b. As the studs 18 may be displaced along the length of the slots 19, the length of the narrow connecting member 12 may be adjusted.

The orthosis according to the invention may be integrally formed from a thermoplastic material forming a matrix 20, FIG. 9, in which the above mentioned layers of reinforcing fibres are embedded. The matrix and fibre materials may be positioned in the desired pattern between a pair of plastic films 21 and the space between the films may be sealed and evacuated by connecting such sealed space to a vacuum source, for example in an evacuation and sealing device 22 diagrammatically shown in FIG. 9. Thereafter, a sample 23 thus made may be formed into the desired shape, preferably in a mould 24 having a stiff wall defining the desired shape of the article, and a flexible mould wall, such as a cloth. The desired shape of the article may then be obtained by connecting the mould cavity to a vacuum source, not shown. The shaped sample or article may then be solidified by heating the article to a fusing or softening temperature of the thermoplastic matrix material and subsequently cooling. Such heating and cooling preferably takes place in the mould 24 in which the sample is formed into the desired shape. The plastic films 21 may have a melting or softening temperature equal to or lower than that of the matrix material so that the film material may migrate into the matrix material. Alternatively, the softening or melting temperature of the material of the films may be higher than that of the matrix material, so that the films may form a skin of the final product.

It should be understood that various changes and modifications of the embodiment described above with reference to the drawings may be made without departing from the scope of the present invention as defined in the following claims.

What is claimed is:

1. An ankle-foot orthosis made from a thin, shaped, light weight, thermoplastic material with reinforcing fibers, said orthosis comprising:
   a flat foot-supporting member including an arch part located between a rear, heel supporting part and a front, ball supporting part, the heel supporting part being more flexible than the ball supporting part;
   a calf abutment member;
   a narrow connecting member connected to the arch part of the foot-supporting member and extending from a location at one side of the foot-supporting member to the calf abutment member so as to interconnect the foot-supporting member and the calf abutment member, the connecting member being substantially more stiff than the foot-supporting member; and
   a releasable fastener for fastening the calf abutment member to a leg of the user.

2. An orthosis according to claim 1, wherein the narrow connecting member extends along a substantially helical path.

3. An orthosis according to claim 1, wherein the narrow connecting member is widening towards the calf abutment member, which is arched so as to define a calf abutment surface having a substantially calf-complementary shape.

4. An orthosis according to claim 1, wherein the releasable fastener comprises a strap for interconnecting opposite ends of the calf abutment member.

5. An orthosis according to claim 1, wherein the reinforcing fibres are selected from the group consisting of carbon fibers and glass fibers.

6. An orthosis according to claim 1, wherein the ball supporting part contains more layers of reinforcing fibers than the heel supporting part.

7. An orthosis according to claim 1, wherein the connecting member contains more layers of reinforcing fibers than the heel and ball supporting parts of the foot-supporting member.

8. An orthosis according to claim 1, wherein layers of reinforcing fibers extending longitudinally within the connecting member continue into the arch part of the foot-supporting member.

9. An orthosis according to claim 1, wherein the thermoplastic material is selected from the group consisting of polyethylene, polypropylene, modified polyethylene terepthalate, polyamide, polyethylene terepthalate, wherein the desired shape is formed in a mold, in which the blank is subsequently heated to a polyether imide, polyether sulfone, and polyether ketone.

10. An orthosis according to claim 1, which is made as a single integral part.

11. An orthosis according to claim 1, wherein the narrow connecting member is divided into two parts, which may be releasably interconnected by releasable connecting means.

12. An orthosis according to claim 11, wherein the connecting means allow the length of the connecting member to be adjusted.

13. A method of making an orthosis made of a light weight material and having a flat, foot-supporting member for extending beneath the sole of a foot of a user, a calf abutment member for abutting the calf of the user, a narrow connecting member extending from the foot-supporting member at a location on one side of the of the ankle of the user to the calf abutment member so as to interconnect the foot-supporting member and the calf abutment member, and a releasable fastener for fastening the calf abutment member to a leg of the user, said method comprising:
   positioning a thermoplastic material and reinforcing fibers between opposite plastic films in a desired mutual arrangement;
   sealing the space defined between the opposite films;
   removing air or gas from said sealed space so as to compact the material arranged therein so as to form a blank;
   arranging the blank in a mold cavity defined between a pair of first and second mold surfaces, the first mold surface defining the desired shape being formed by a relatively stiff mold wall and the second mold surface being formed by a flexible wall;
   heating the blank to a plasticizing temperature;
   connecting the mold cavity being connected to a vacuum source so as to form the blank into the desired shape; and
   subsequently cooling the shaped blank.

14. A method according to claim 13, wherein the melting point of the films is equal to or lower than that of the thermoplastic material positioned therebetween.

* * * * *